(12) United States Patent
Jaffe

(10) Patent No.: US 11,338,064 B2
(45) Date of Patent: May 24, 2022

(54) BIOLOGICAL VALVE FOR VENOUS INSUFFICIENCY

(71) Applicant: enVVeno Medical Corporation, Irvine, CA (US)

(72) Inventor: Norman Jaffe, Dana Point, CA (US)

(73) Assignee: enVVeno Medical Corporation, Irvine, CA (US)

( * ) Notice: Subject to any disclaimer, the term of this patent is extended or adjusted under 35 U.S.C. 154(b) by 0 days.

(21) Appl. No.: 17/323,238

(22) Filed: May 18, 2021

(65) Prior Publication Data

US 2021/0268153 A1 Sep. 2, 2021

Related U.S. Application Data

(63) Continuation of application No. 15/711,314, filed on Sep. 21, 2017, which is a continuation of application
(Continued)

(51) Int. Cl.
| | | |
|---|---|---|
| *A61F 2/24* | (2006.01) | |
| *A61L 27/50* | (2006.01) | |
| *A61L 27/36* | (2006.01) | |

(52) U.S. Cl.
CPC .......... *A61L 27/507* (2013.01); *A61F 2/2412* (2013.01); *A61F 2/2415* (2013.01); *A61F 2/2475* (2013.01); *A61L 27/3625* (2013.01)

(58) Field of Classification Search
CPC ........ A61F 2/2475; A61F 2/24; A61F 2/2412; A61F 2/2415
See application file for complete search history.

(56) References Cited

U.S. PATENT DOCUMENTS

| | | | |
|---|---|---|---|
| 3,983,581 A | | 10/1976 | Angell et al. |
| 4,218,782 A | * | 8/1980 | Rygg ............... A61F 2/2415 623/2.15 |

(Continued)

FOREIGN PATENT DOCUMENTS

| | | |
|---|---|---|
| EP | 0850607 | 7/1998 |
| WO | WO8800459 | 1/1988 |

(Continued)

OTHER PUBLICATIONS

García-Rinaldi R, Soltero E, Gaviria J, Sosa J, Tucker P. Implantation of cryopreserved allograft pulmonary monocusp patch to treat nonthrombotic femoral vein incompetence. Tex Heart Inst J. 2002;29(2):92-9. PMID: 12075883; PMCID: PMC116733. (Year: 2002).*

(Continued)

*Primary Examiner* — Seema Mathew
(74) *Attorney, Agent, or Firm* — Kramer Levin Naftalis & Frankel LLP

(57) ABSTRACT

A bioprosthetic valve for repairing a deep venous insufficiency in a subject includes a single leaflet from a xenogeneic heart valve attached at natural margins of attachment to a patch of valve wall tissue. The patch may extend axially above and below the leaflet and circumferentially on either side of the leaflet to provide a region for attaching the patch to a fenestration in a host vein. A bioprosthetic valve may be manufactured by excising a portion of a xenogeneic heart valve including a single leaflet and contiguous wall tissue, and may further comprise shaving off excess leaflet tissue from adjacent leaflets. A method of replacing a malfunctioning venous valve in a subject includes providing a bioprosthetic valve as described above and inserting it to the host vein.

14 Claims, 7 Drawing Sheets

Related U.S. Application Data

No. 12/789,176, filed on May 27, 2010, now abandoned, which is a continuation of application No. 12/252,253, filed on Oct. 15, 2008, now abandoned.

(60) Provisional application No. 60/980,708, filed on Oct. 17, 2007.

(56) References Cited

U.S. PATENT DOCUMENTS

| | | | |
|---|---|---|---|
| 4,247,292 A | | 1/1981 | Angell |
| 4,345,340 A | | 8/1982 | Rosen |
| 4,350,492 A | * | 9/1982 | Wright .................. A61F 2/2415 8/94.11 |
| 4,364,126 A | | 12/1982 | Rosen |
| 4,506,394 A | | 3/1985 | Bedard |
| 4,535,483 A | | 8/1985 | Klawitter et al. |
| 4,666,442 A | | 5/1987 | Arru et al. |
| 4,692,164 A | * | 9/1987 | Dzemeshkevich ... A61F 2/2412 623/2.14 |
| 4,755,593 A | | 7/1988 | Lauren |
| 4,798,611 A | | 1/1989 | Freeman |
| 4,851,000 A | | 7/1989 | Gupta |
| 5,037,434 A | | 8/1991 | Lane |
| 5,178,633 A | | 1/1993 | Peters |
| 5,352,240 A | | 10/1994 | Ross |
| 5,549,665 A | | 8/1996 | Vesely et al. |
| 5,554,185 A | | 9/1996 | Block et al. |
| 5,595,571 A | | 1/1997 | Jaffe et al. |
| 5,607,465 A | * | 3/1997 | Camilli .................. A61F 2/2418 604/104 |
| 5,713,953 A | | 2/1998 | Vallana et al. |
| 5,716,417 A | * | 2/1998 | Girard .................. A61F 2/2418 623/2.38 |
| 5,720,777 A | | 2/1998 | Jaffe et al. |
| 5,843,180 A | | 12/1998 | Jaffe et al. |
| 5,843,181 A | | 12/1998 | Jaffe et al. |
| 5,855,602 A | * | 1/1999 | Angell .................. A61F 2/2412 623/2.11 |
| 5,865,723 A | | 2/1999 | Love |
| 6,059,827 A | | 5/2000 | Fenton |
| 6,165,216 A | * | 12/2000 | Agathos ................ A61F 2/2412 623/2.13 |
| 6,168,614 B1 | | 1/2001 | Andersen et al. |
| 6,174,331 B1 | | 1/2001 | Moe et al. |
| 6,183,512 B1 | | 2/2001 | Howanec et al. |
| 6,383,732 B1 | | 5/2002 | Stone |
| 6,461,382 B1 | | 10/2002 | Cao |
| 6,482,228 B1 | | 11/2002 | Norred |
| 6,517,576 B2 | * | 2/2003 | Gabbay .................. A61F 2/2412 33/511 |
| 6,558,418 B2 | | 5/2003 | Carpentier et al. |
| 6,761,735 B2 | | 7/2004 | Eberhardt et al. |
| 7,172,625 B2 | | 2/2007 | Shu et al. |
| 7,247,167 B2 | | 7/2007 | Gabbay |
| 7,323,010 B2 | | 1/2008 | Verona et al. |
| 7,399,315 B2 | | 7/2008 | Iobbi |
| 7,556,645 B2 | | 7/2009 | Lashinski et al. |
| 7,618,447 B2 | | 11/2009 | Case et al. |
| 2001/0039450 A1 | | 11/2001 | Pavcnik et al. |
| 2002/0072794 A1 | | 6/2002 | Gabbay |
| 2003/0023302 A1 | | 1/2003 | Moe et al. |
| 2003/0191525 A1 | * | 10/2003 | Thornton .............. A61F 2/2475 623/1.24 |
| 2004/0098098 A1 | | 5/2004 | McGuckin et al. |
| 2005/0055079 A1 | * | 3/2005 | Duran .................... A61F 2/243 623/1.13 |
| 2005/0075724 A1 | | 4/2005 | Svanidze et al. |
| 2005/0075726 A1 | | 4/2005 | Svanidze et al. |
| 2005/0273159 A1 | * | 12/2005 | Opie ...................... A61F 2/2475 623/1.24 |
| 2006/0184239 A1 | | 8/2006 | Andrieu et al. |
| 2006/0210597 A1 | | 9/2006 | Hiles |
| 2006/0265053 A1 | * | 11/2006 | Hunt ...................... A61F 2/2412 623/1.24 |
| 2007/0038295 A1 | * | 2/2007 | Case ...................... A61F 2/2475 623/2.18 |
| 2007/0208417 A1 | * | 9/2007 | Agnew .................. A61F 2/2418 623/1.24 |
| 2007/0288086 A1 | | 12/2007 | Kalmann et al. |
| 2007/0288087 A1 | | 12/2007 | Gabbay |
| 2008/0133005 A1 | | 6/2008 | Andrieu et al. |
| 2008/0243246 A1 | | 10/2008 | Ryan et al. |
| 2008/0288055 A1 | * | 11/2008 | Paul, Jr. ................ A61F 2/2475 623/1.24 |
| 2009/0018649 A1 | | 1/2009 | Jaffe et al. |
| 2009/0254176 A1 | * | 10/2009 | Butera .................. A61F 2/2418 623/1.24 |
| 2010/0234939 A1 | | 9/2010 | Jaffe |
| 2018/0133004 A1 | * | 5/2018 | Montoya .................. A61F 2/06 |

FOREIGN PATENT DOCUMENTS

| | | |
|---|---|---|
| WO | WO9014804 | 12/1990 |
| WO | WO9640008 | 12/1996 |
| WO | WO0067661 | 11/2000 |
| WO | WO0067679 | 11/2000 |
| WO | WO06092648 | 9/2006 |
| WO | WO08035337 | 3/2008 |
| WO | WO08150529 | 12/2008 |

OTHER PUBLICATIONS

Garcia-Rinaldi R, Revuelta JM, Martinez MJ, Granda E, De Santos L. Femoral vein valve incompetence: treatment with a xenograft monocusp patch. Preliminary report. J Vasc Surg. Jun. 1986;3(6):932-5. PMID: 3712639. (Year: 1986).*

Michael C. Dalsing, MD, et al.: "A Multicenter, Phase I Evaluation of Cryopreserved Venous Valve Allografts for the Treatment of Chronic Deep Venous Insufficiency," Journal of Vascular Surgery, vol. 30, No. 5, Nov. 1999, pp. 854-866.

Wei-Hsin Tien, PhD., et al.: "Role of Vessel-to-Prosthesis Size Mismatch in Venous Valve Performance," Journal of Vascular Surgery: Venous and Lymphatic Disorders, May 2016, 10 pages.

Daniel Edward Tanner, Design, Analysis, Testing, and Evaluation of a Prosthetic Venous Value, a Thesis Presented to the Academic Faculty, Georgia Institute of Technology, May 2013, 158 pages.

Duran, C; Revuelta, J.; Pomar, J.; A new composite xenograft monocusp patch for reconstruction of hte right ventricular outflow tract: A preliminary report. Cardiovascular Diseases, Bulletin of the Texas Heart Institute, Mar. 1980, 7: 58-65. (Year: 1980).

Garcia-Rinaldi, R.; Revuelta, J.M.; Martinez, M.J.; Granda, E.; De Santos, L.; Femoral vein valve incompetence: Treatment with a xenograft monocusp patch. Journal of Vascular Surgery, Jun. 1986, 3: 932-935. (Year: 1986).

Brown et al., "Right ventricular outflow tract reconstruction with a polytetrefluoroethylene monocusp valve: a twelve-year experience", The Journal of Thoracic and Cardiovascular Surgery, pp. 1336-1343, May 2007.

Roughneen et al., "The Pericardial Membrane Pulmonary Monocusp: Surgical Technique and Early Results", Journal of Cardiovascular Surgery, vol. 14, pp. 370-374, 1999.

Rinaldi et al., "Implantation of Cryopreserved Allograft Pulmonary Monocusp Patch", Texas Heart Institute Journal, vol. 29, No. 2, pp. 92-99, 2002.

* cited by examiner

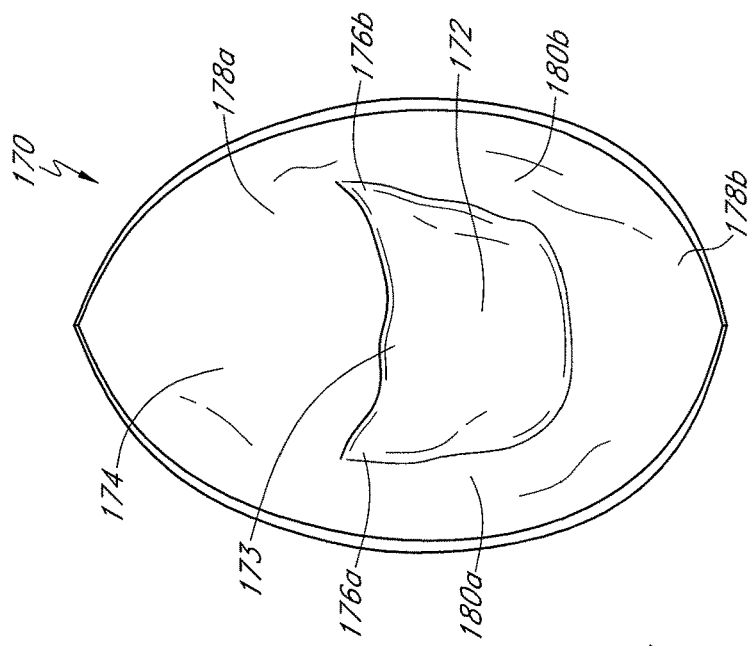
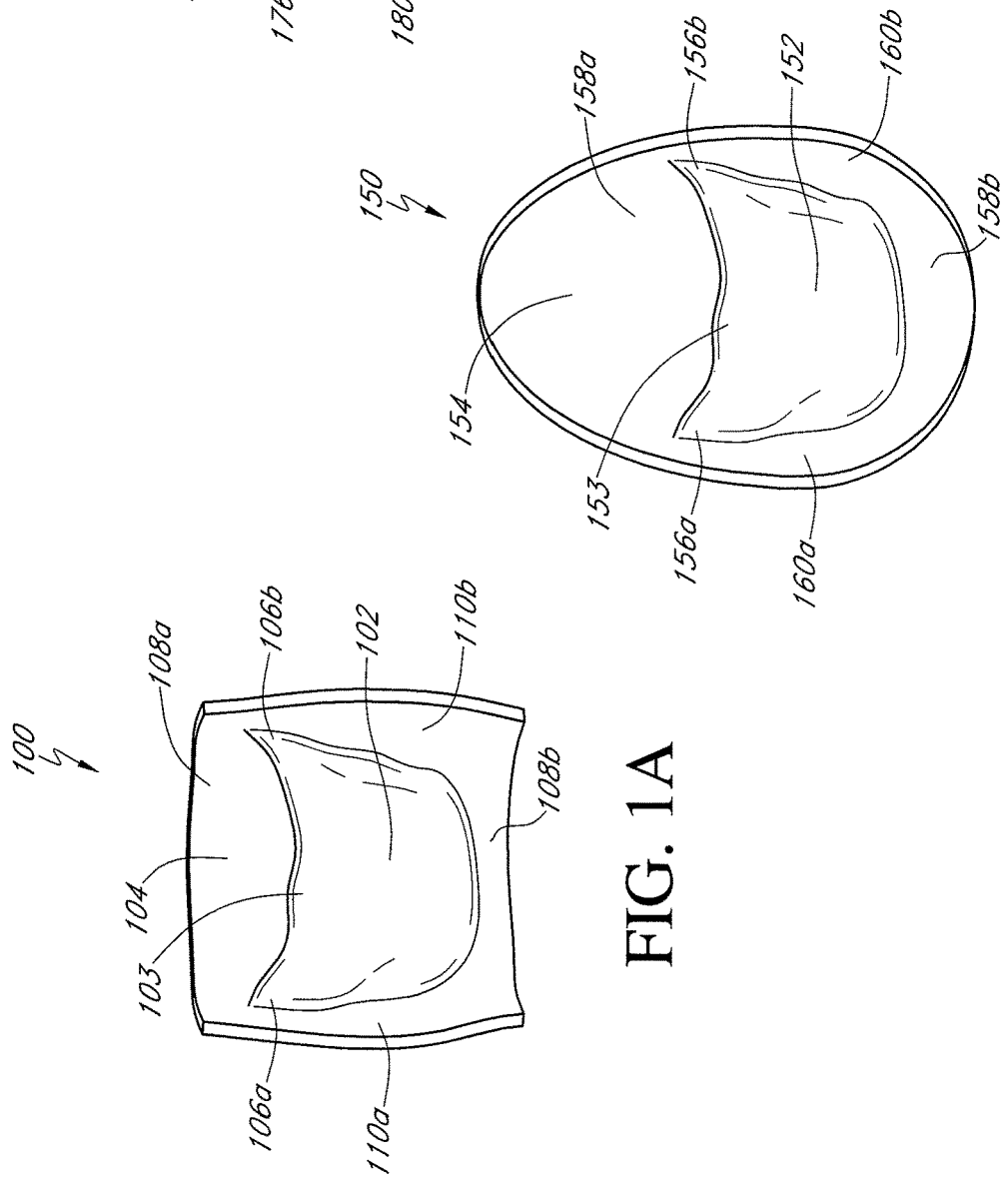
FIG. 1A
FIG. 1B
FIG. 1C

BIOLOGICAL VALVE FOR VENOUS INSUFFICIENCY

CROSS-REFERENCE TO RELATED APPLICATIONS

This application is a continuation of U.S. application Ser. No. 15/711,314, filed Sep. 21, 2017, which is a continuation of U.S. application Ser. No. 12/789,176, filed May 27, 2010, which is a continuation of U.S. application Ser. No. 12/252,253, filed Oct. 15, 2008, which claims the benefit of U.S. Provisional Application No. 60/980,708, filed Oct. 17, 2007, the entire disclosure of each of which is hereby incorporated by reference.

BACKGROUND OF THE INVENTION

Field of the Invention

This application generally relates to a biological valve for the replacement of a venous valve of the deep venous system of the leg or other veins of comparable caliber.

Description of the Related Art

Patients with chronic deep vein insufficiency may require the repair or replacement of at least one of the venous valves of the deep veins of the leg. Also, in some cases the venous valve replacement may involve the iliac veins.

Present therapy involves either the surgical repair of the valve leaflets or external banding of the vein to decrease the diameter and bring the weakened leaflets to a geometry which may allow for improved function. The incompetent venous valves of patients with advanced chronic disease are usually not amenable to repair and may be replaced.

Currently, venous valve replacement and therapy is limited to allograft or cryopreserved valves. Allograft valves are difficult to harvest and cryopreserved valves can elicit a deleterious immune response.

SUMMARY OF EXEMPLARY EMBODIMENTS

In accordance with one embodiment, a monocusp bioprosthetic valve for implantation into a host vein of a subject is described. The bioprosthetic valve comprises biological tissue from a xenogeneic source. The biological tissue comprises a single leaflet from a heart valve and a patch comprising tissue contiguous with the single leaflet. In one aspect of the embodiment, the xenogeneic source is porcine. In a further aspect, the single leaflet is attached to the patch at natural margins of attachment. In a still further aspect, the heart valve is an aortic valve. In such an aspect, the patch may include a segment of the aortic annulus. In the same aspect, the single leaflet may be a noncoronary leaflet. In yet another aspect of the embodiment, the patch has a generally rectangular shape. In a further aspect, the patch has a generally ovoid shape. In a still further aspect, the patch extends circumferentially on either side of the leaflet so as to provide a region for attachment to the host vein. In another aspect, the patch extends axially above and below the leaflet so as to provide a region for attachment to the host vein. In any of these aspects, at least a portion of the patch may be covered with a synthetic fabric. Also, in any of these aspects, the subject may be human.

In accordance with another embodiment, a bioprosthetic valve for implantation into a host vein of a subject consisting essentially of a single leaflet from a xenogeneic heart valve attached at natural margins of attachment to a patch of valve wall tissue from the xenogeneic heart valve is provided. In one aspect of this embodiment, the xenogeneic heart valve is porcine. In a further aspect, the patch extends circumferentially on either side of the leaflet to provide a region for attachment to the host vein. In another aspect, the patch extends axially above and below the leaflet to provide a region for attachment to the host vein. In yet another aspect, the xenogeneic heart valve is an aortic valve. In the preceding aspect, the leaflet may be a noncoronary leaflet.

In accordance with yet another embodiment, a method of manufacturing a replacement venous valve for a subject is described. The method comprises providing a xenogeneic heart valve which has at least one leaflet and a valve wall, and which has been subjected to a fixation treatment. The method further comprises excising a portion of the heart valve. The portion comprises at least a selected leaflet attached at natural margins of attachment to a patch of valve wall tissue, such that said excised portion comprises a single leaflet. In one aspect of the embodiment, the xenogeneic heart valve is porcine. In another aspect, the patch extends circumferentially on either side of the selected leaflet to provide a region for attachment to the host vein. In a further aspect, the patch extends axially above and below the selected leaflet to provide a region for attachment to the host vein. In a still further aspect, the xenogeneic heart valve is an aortic valve. In such an aspect, the selected leaflet may be a noncoronary leaflet. In yet another aspect of the embodiment, the method further comprises cutting through each of the natural commissures and shaving off tissue of any leaflets adjacent to the selected leaflet. In any of these aspects, the subject may be human.

In accordance with a further embodiment, a method of treating a malfunctioning valve in a host vein of a subject is described. The method comprises providing a replacement biological valve comprising a single leaflet from a xenogeneic heart valve attached at natural margins of attachment to a patch of contiguous tissue from the xenogeneic heart valve. The method further comprises inserting said replacement biological valve into said host vein. In one aspect of the embodiment, the method further comprises creating a fenestration in the host vein in the region of the malfunctioning valve, the fenestration having a shape generally corresponding to the patch. In the preceding aspect, the fenestration may be created generally in the region of the malfunctioning valve, generally above the region of the malfunctioning valve, or generally below the region of the malfunctioning valve. In the same aspect, the method may further comprise attaching the replacement biological valve to the host vein at the fenestration. In another aspect, the method further comprises removing at least one leaflet from the malfunctioning valve of the host vein. In a further aspect, the xenogeneic heart valve is a porcine aortic valve. In such an aspect, the single leaflet may be a noncoronary leaflet. In a still further aspect, the leaflet and patch have been subjected to a fixation treatment. In such an aspect, the fixation treatment may include exposing the leaflet and patch to glutaraldehyde solution. In any of these aspects, the subject may be human.

BRIEF DESCRIPTION OF THE DRAWINGS

FIG. 1A is a front perspective view of a bioprosthetic valve according to an embodiment.

FIG. 1B is a front perspective view of a bioprosthetic valve according to an alternative embodiment.

FIG. 1C is a front perspective view of a bioprosthetic valve according to a further embodiment.

DETAILED DESCRIPTION OF CERTAIN INVENTIVE ASPECTS

Figure 1F:
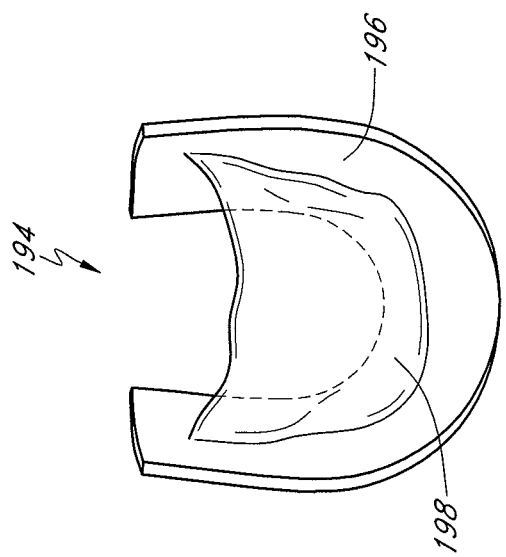
FIG. 1F is a front perspective view of a bioprosthetic valve according to a further embodiment.

The features, aspects and advantages of the present invention will now be described with reference to the drawings of various embodiments, which are intended to be within the scope of the invention herein disclosed. These and other embodiments will become readily apparent to those skilled in the art from the following detailed description of the embodiments having reference to the attached figures, the invention not being limited to any particular embodiment(s) disclosed.

Various embodiments provide a replacement venous valve comprising a single biological valve leaflet configured to function under low-flow, low-pressure conditions of the deep venous system. Embodiments advantageously utilize the structural properties of biological valve leaflet tissue, preferably xenogeneic aortic valve leaflet tissue, to provide a replacement venous valve offering hemodynamics matching the hemodynamics of the veins of the lower extremities.

Embodiments using tissue from an aortic valve in particular also take advantage of the unique shape of the aortic sinus to mimic the natural flexibility and curvature of a normally functioning vein in the region of a venous valve. These and other embodiments provide a desirable geometry for opening and closing of a bioprosthetic valve in a host vein, providing sufficient obstruction of the host vein in the closed position and allowing for improved washing of the leaflet surface when the bioprosthetic valve is opened.

Certain embodiments incorporate a noncoronary leaflet of an aortic valve in a bioprosthetic valve, desirably providing a "clean" leaflet containing significant amounts of collagen and elastin with minimal muscle tissue attached thereto. Further, as the unique configuration of the aortic wall in the region of the noncoronary leaflet includes no exiting coronary arteries, these and other embodiments offer a continuous surface for use as a patch in the wall of the host vein.

A Bioprosthetic Valve

With reference now to FIG. 1A, a bioprosthetic valve 100 according to an embodiment is illustrated. The bioprosthetic valve 100 generally includes a single leaflet 102 attached to a patch 104 at natural commissures 106(a), 106(b). The leaflet 102 has a free edge 103 which responds to differing pressures in the host vein to open and close the valve 100.

As shown in the figure, the patch 104 may extend axially (with respect to the source vessel and the host vein) above and below the leaflet 102 to provide upper and lower regions 108(a), 108(b) for attaching the bioprosthetic valve 100 to a host vein. Thus, in embodiments using an aortic valve source, the patch 104 may include a segment of the aortic annulus and/or a segment of the aortic wall.

The patch 104 may also extend circumferentially on either side of the leaflet 102, to provide lateral regions 110(a), 110(b) for attaching the bioprosthetic valve 100 to a host vein. The regions 110(a), 110(b) may extend only minimally beyond the region of the leaflet 102, as shown in FIG. 1, or may extend further so as to partially or entirely encircle the host vein upon implantation. The patch 104 may be generally rectangular, as shown in FIG. 1, or may have any other suitable shape (such as circular, oval, or oblong) for implantation into a host vein. Although illustrated with the regions 108(a), 108(b) and 110(a), 110(b) extending substantially symmetrically above and below and on either side of the leaflet 102, the patch 104 can of course extend about the leaflet 102 by different lengths in different directions.

The bioprosthetic valve 100 and its component leaflet 102 may be selected and configured so that, with the valve 100 in a closed position, the leaflet 102 provides adequate obstruction of the host vein at or near the site of the malfunctioning venous valve. The leaflet 102 need not completely obstruct the host vein in the closed position, however, as some degree of backflow is acceptable in the venous system. Accordingly, with the valve 100 in a closed position, the free edge 103 of the leaflet 102 may (but need not) contact an opposite wall of the host vein continuously along the length of the free edge 103.

The bioprosthetic valve 100 may comprise tissue from any suitable xenogeneic source, such as a porcine, bovine, or equine heart valve. The leaflet 102 may comprise a single leaflet from a heart valve, such as a noncoronary leaflet of an aortic valve. The patch 104 may comprise valve wall tissue which is contiguous with the leaflet. In certain embodiments, the patch 104 may include a segment of the aortic annulus and/or a segment of the aortic wall from the source valve. The patch 104 may include part or all of that portion of the aortic wall which defines the natural sinus for the leaflet 102. Including a portion of the natural sinus advantageously provides a spatial buffer between the leaflet 102 and the valve wall when the valve 100 is in the open position, both preventing or reducing adherence of the leaflet 102 to the valve wall and facilitating closing of the valve 100 when flow pressure is reduced. Additionally, the patch 104 may be partially or entirely covered with a synthetic liner, such as a flexible synthetic fabric as shown in FIG. 1H. Additionally or alternatively, the patch 104 may be sewn or otherwise attached to a larger backing or liner, or to a conduit or tube configured for attachment to an external surface of the native vein as shown in FIG. 1G. Such a backing or conduit can be used to coarct the vessel or otherwise remodel the vessel wall. Such a backing or conduit may comprise a flexible biological and/or nonbiological material, depending on the needs of the particular application.

With reference now to FIG. 1B, a bioprosthetic valve 150 according to an alternative embodiment is illustrated. The valve 150 has a single leaflet 152 attached to a patch 154 at natural margins of attachment 156(a), 156(b). The leaflet 152 has a free edge 153 which responds to differing pressures in the host vein to open and close the valve 150.

The patch 154 has a generally ovoid shape which extends axially (with respect to the source vessel and the host vein) above and below the leaflet 152 to provide upper and lower regions 158(a), 158(b) for attaching the bioprosthetic valve 150 to a host vein. The patch 154 also extends circumferentially on either side of the leaflet 152, to provide lateral regions 160(a), 160(b) for attaching the bioprosthetic valve 150 to a host vein.

With reference now to FIG. 1C, a bioprosthetic valve 170 according to a further embodiment is illustrated. The valve 170 has a single leaflet 172 attached to a patch 174 at natural margins of attachment 176(a), 176(b). The leaflet 172 has a free edge 173 which responds to differing pressures in the host vein to open and close the valve 170.

The patch 174 has a generally lenticular shape which extends axially (with respect to the source vessel and the host vein) above and below the leaflet 172 to provide upper and lower regions 178(a), 178(b) for attaching the bioprosthetic valve 170 to a host vein. The patch 174 also extends circumferentially on either side of the leaflet 172, to provide lateral regions 180(a), 180(b) for attaching the bioprosthetic valve 170 to a host vein. As shown in the figure, the upper and lower regions 178(a), 178(b) may include pointed or angled sections allowing a practitioner to secure the valve 170 in an appropriate position and then use a continuous stitching pattern to close the anastomosis.

Figure 1E:
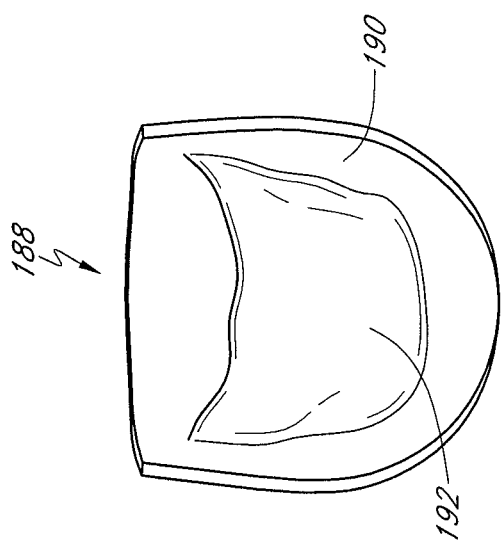
FIG. 1E is a front perspective view of a bioprosthetic valve according to another alternative embodiment.
Figure 1D:
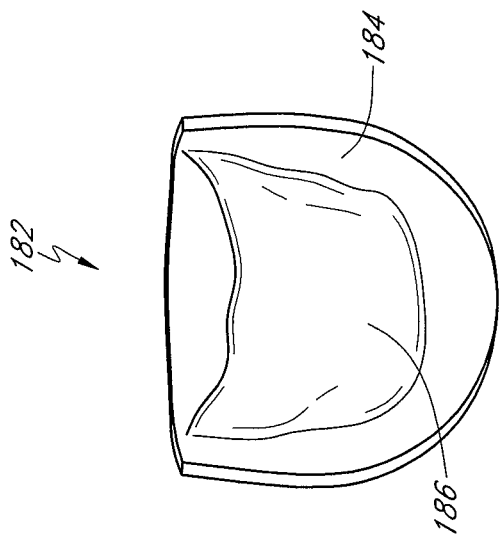
FIG. 1D is a front perspective view of a bioprosthetic valve according to another alternative embodiment.
Figure 1G:
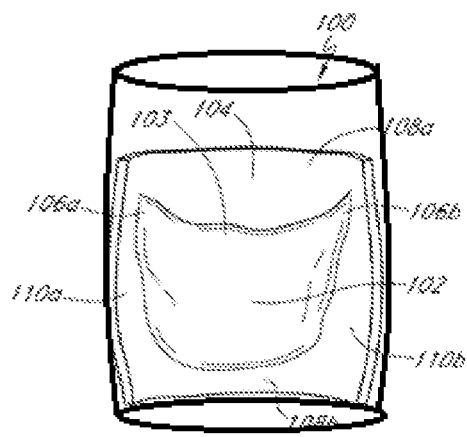
FIG. 1G is a front perspective view of a bioprosthetic valve according to a further embodiment.
Figure 1H:
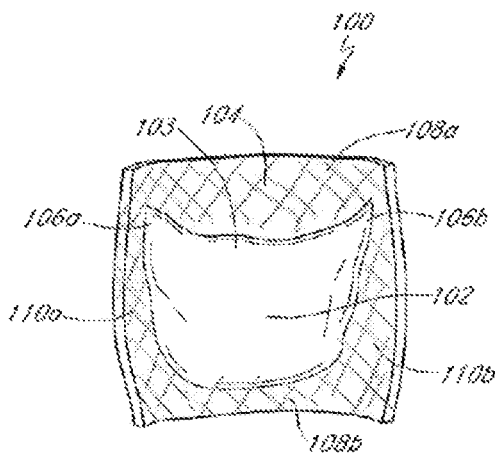
FIG. 1H is a front perspective view of a bioprosthetic valve according to a further embodiment.

FIGS. 1D-1F illustrate additional embodiments. FIG. 1D shows a bioprosthetic valve 182 having a single leaflet 186 attached to a patch 184. As shown in the figure, the patch 184 has a shape that generally follows the contour of the interface between the leaflet 186 and the source valve wall. Below the leaflet 186 and circumferentially on either side of the leaflet 186, the patch 184 extends beyond this contour to provide an attachment region for the valve 182. Above the leaflet, the patch 184 extends axially to approximately the same height as the leaflet 186 in an open position, so as to avoid interaction between the leaflet 186 and the natural wall of the host vessel. FIG. 1E shows a bioprosthetic valve 188 having a single leaflet 192 attached to a patch 190. The patch 190 has a similar shape to the patch 184 of FIG. 1D, but extends axially further above the leaflet 192. The patch 190 can thus include part or all of the tissue that defines the natural sinus for the leaflet 192. FIG. 1F shows a bioprosthetic valve 194 having a single leaflet 198 attached to a substantially U-shaped patch 196. The patch 196 includes the natural interface between the leaflet 198 and the source valve wall and extends slightly beyond this interface to provide an attachment region for the valve 194, without including the tissue that defines the natural sinus for the leaflet 198.

In these and other embodiments, the inclusion of a contiguous wall portion that includes tissue taken from the donor vessel wall at an attachment region where the leaflet attaches to the vessel wall is considered advantageous at least because the attachment region includes a unique microstructure that is believed to enhance the ruggedness of the bioprosthetic valve. Retaining the natural margins of attachment between the leaflet and vessel wall in the contiguous wall portion is considered particularly advantageous. For example, in an aortic valve, the margins of attachment (i.e., the leaflet anchorages) are composed primarily of a dense collagenous tissue that provides a durable attachment between the leaflet and wall, which is expected to have a beneficial advantage on the longevity of a bioprosthetic valve that includes the margins of attachment.

Making a Bioprosthetic Valve

In some embodiments, after biological heart valve tissue to be used for the replacement valve is first harvested, it may be stored in a preservative solution. The heart valve tissue may then be subjected to a fixation or crosslinking treatment in order to preserve the material from natural decay. Suitable fixation methods include exposing the tissue to a glutaraldehyde solution. Such a solution may comprise, for example, 0.1%-1.0% glutaraldehyde in a buffer, such as a phosphate or citrate buffer, formulated to maintain pH at between 6.0 and 8.0. The tissue may be exposed to such a solution for a few minutes, up to several days, depending on the crosslinking reaction rate for a given solution. The tissue may be fixed in a zero-stress environment. Alternatively, the tissue may be reinforced during fixation so as to preserve or enhance the curvature of the patch tissue or the configuration of the leaflet tissue. Tissue processed using the same procedures used by Hancock-Jaffe Laboratories of Irvine, Calif., to fabricate prosthetic heart valves may be used in the preparation of bioprosthetic valves according to embodiments of the present invention. After crosslinking, the tissue can optionally be irradiated according to known procedures with high energy X-radiation or gamma radiation, in an amount sufficient to sterilize the tissue without significantly decreasing its tensile strength, so as to render the tissue more flexible and compliant, and less antigenic. For example, in some embodiments, the irradiation procedures provided in U.S. Pat. No. 4,798,611, the disclosure of which is incorporated herein by reference in its entirety, may be used. Next, a desired leaflet may be selected for use in a bioprosthetic valve, and a portion of the heart valve including at least the entire selected leaflet may be excised from the valve.

Figure 2:
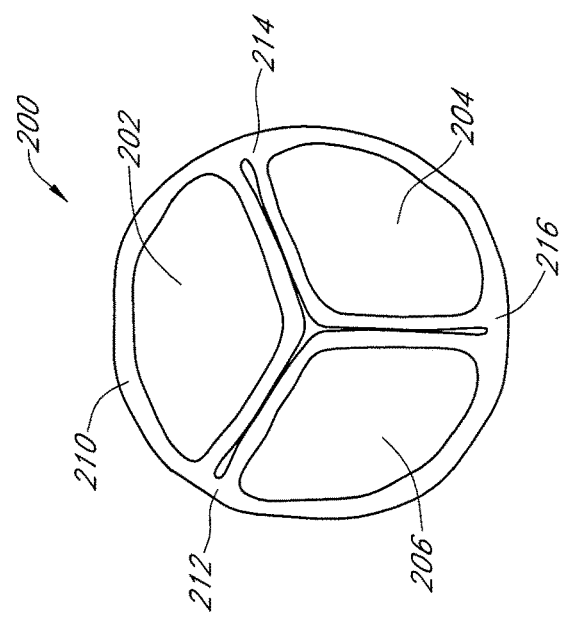
FIG. 2 is an axial cross-sectional view of an aortic valve in closed position, illustrating the trileaflet configuration of the aortic valve.

FIG. 2 illustrates an aortic valve 200 which may be used in various embodiments. As shown in FIG. 2, the aortic valve 200 has a trileaflet configuration comprising a selected leaflet 202 and neighboring leaflets 204 and 206. The selected leaflet 202 may, for example, be the noncoronary leaflet of the aortic valve 200, which tends to be the cleanest of the leaflets (i.e., tends to have the least muscle) and also has the most predictable shape. The leaflets 202, 204, and 206 are attached to a valve wall 210 at natural commissures 212, 214, and 216.

Figure 3:
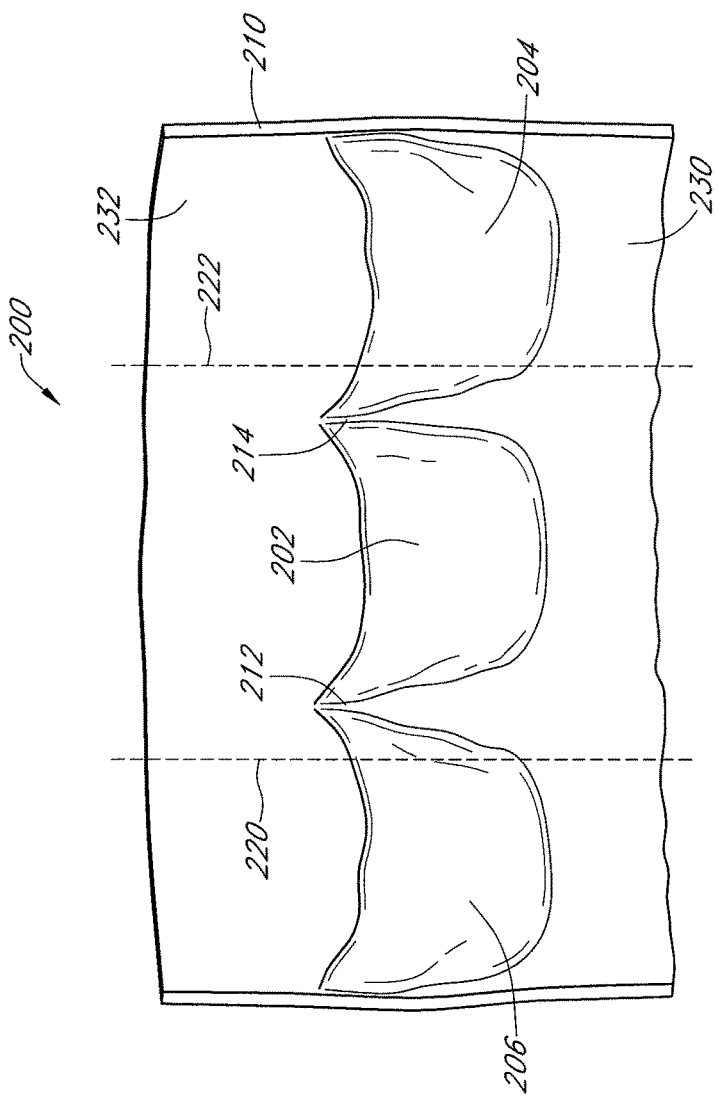
FIG. 3 is a front view of the aortic valve of FIG. 2 showing the valve cut along a commissure and laid open.

Referring now to FIG. 3, the aortic valve 200 of FIG. 2 is shown cut along the commissure 216 and laid open to better illustrate the three leaflets 202, 204, and 206. According to various embodiments, the valve wall 210 and the leaflets 204, 206 may be cut, for example along lines 220, 222, to separate the selected leaflet 202 and its contiguous valve wall tissue from the neighboring leaflets 204, 206. As can be seen by the position of the lines 220, 222 in FIG. 3, the excised portion may include a portion of the valve wall 210 extending circumferentially on either side of the selected leaflet 202, so as to provide attachment surfaces comprising valve wall tissue on either side of the leaflet 202. The excised portion may include a portion of the aortic annulus 230 and/or a portion of the aortic wall 232. Next, the commissures 212, 214 of the selected leaflet 202 may be sliced through and the tissue of the adjacent leaflets 204, 206 may be removed, for example by shaving off the adjacent leaflets, leaving the leaflet 202 attached to the aortic wall 232 at its natural margins of attachment. The valve wall tissue which is contiguous with the leaflet 202 may then be further trimmed in any desired shape and configuration suitable for attachment to a host vein, such as, for example, the generally rectangular, generally ovoid, or generally lenticular shapes described above in connection with FIGS. 1A-1C. The thickness of the contiguous wall portion can also be reduced so as to better match the thickness of the host wall, increase compliance, and facilitate attachment of the wall portion to the host vessel (for example by suturing or clipping). Suitable techniques for reducing tissue thickness include shaving, manual dissection, delamination, and other techniques.

Using a Bioprosthetic Valve

Figure 4B:
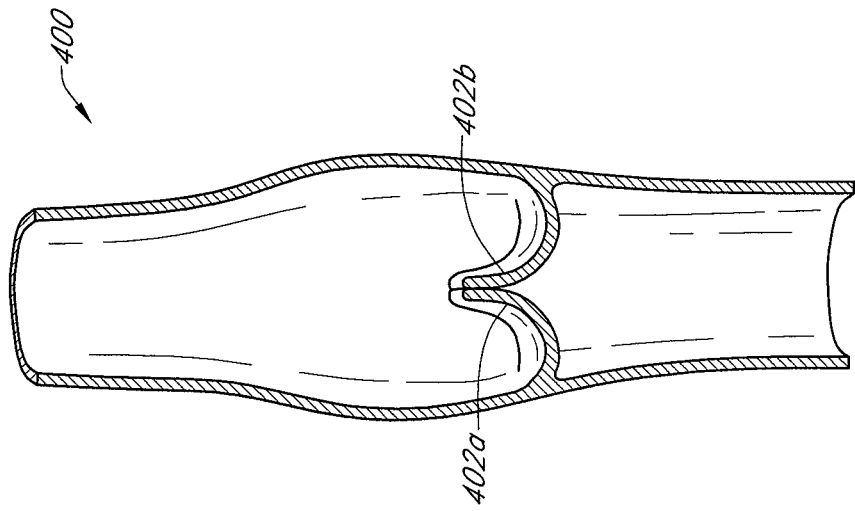
FIG. 4B is a longitudinal cross-sectional view of the vein of FIG. 4A with the valve shown in closed position.
Figure 4A:
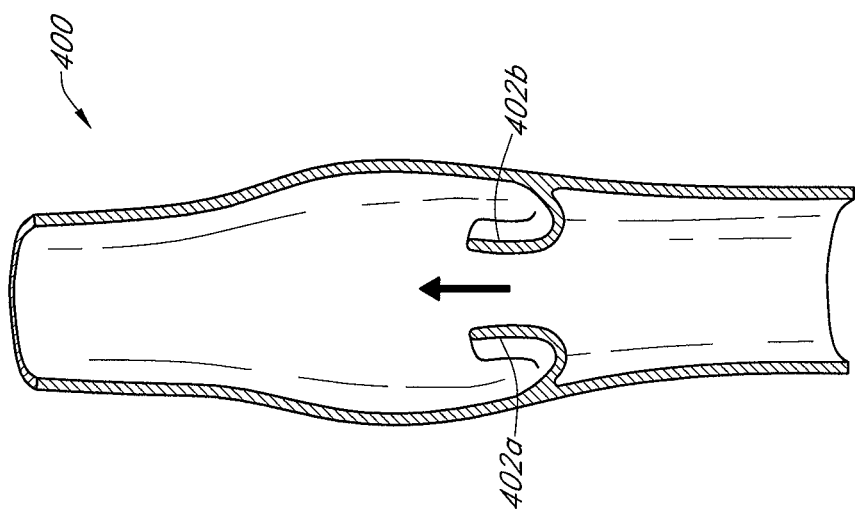
FIG. 4A is a longitudinal cross-sectional view of a vein with a normally functioning venous valve shown in open position.
Figure 5:
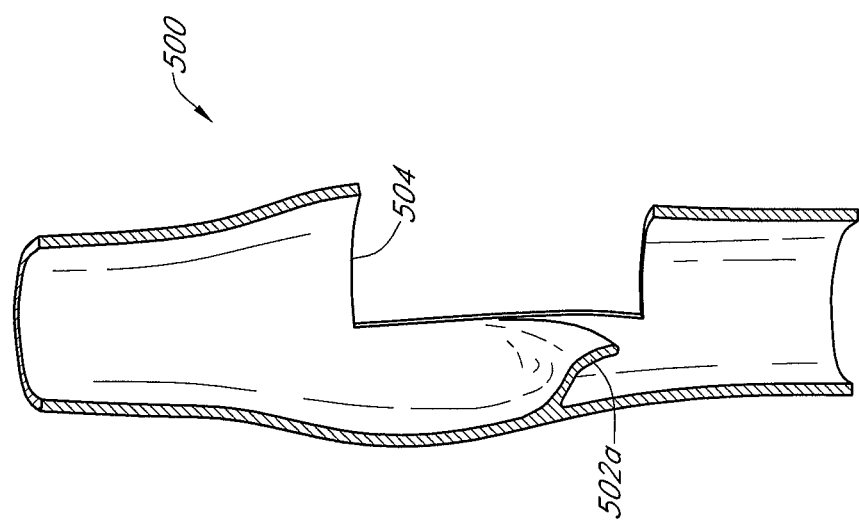
FIG. 5 is a longitudinal cross-sectional view of a vein with a malfunctioning venous valve. The vein is shown with a fenestration in which embodiments of the present invention may be implanted.

With reference now to FIGS. 4A-4B, a normally functioning venous valve 400 is illustrated with valve leaflets 402(*a*), 402(*b*) shown in open (FIG. 4A) and closed (FIG. 4B) positions. FIG. 5, in contrast, illustrates a malfunctioning vein 500 with a non-functioning valve leaflet 502(*a*). A portion of the vein 500, including an opposing valve leaflet (not shown), has been excised to create a fenestration 504 in the region of the incompetent valve leaflets. The fenestration 504 is shown extending through approximately half of the circumference of the vein 500, but may extend through more or less of the vein circumference. Further, although shown in the region of the incompetent native valve of the host vein 500, the fenestration 504 may be cut generally above or generally below the native valve. Additionally, depending on the requirements of the particular application, an entire segment of the malfunctioning vein 500 may be excised to prepare the vein for implantation of various embodiments.

Figure 6:
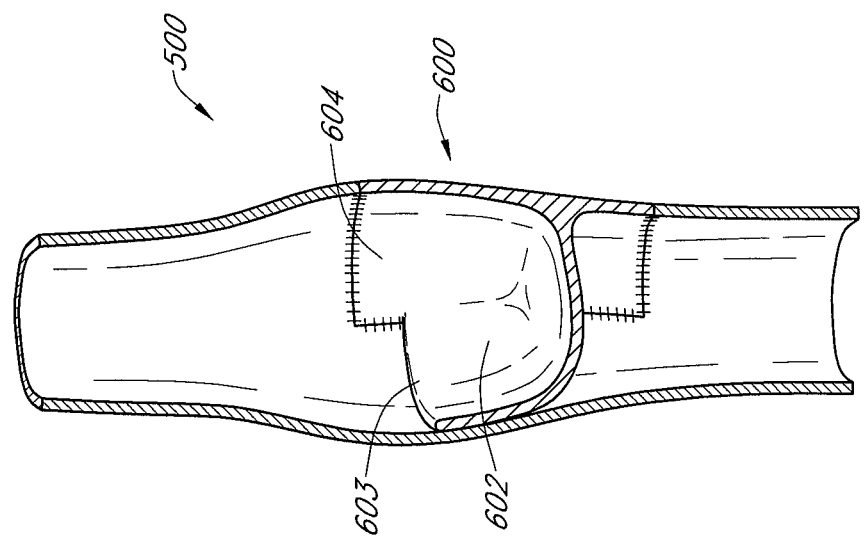
FIG. 6 is a longitudinal cross-sectional view of the host vein of FIG. 5 with an embodiment of the present invention implanted therein.

Referring now to FIG. 6, a bioprosthetic valve 600 according to an embodiment is shown implanted in the host vein 500. The bioprosthetic valve 600 includes a single leaflet 602 from a xenogeneic heart valve attached to a patch 604 of valve wall tissue from the xenogeneic source. The leaflet 602 has a free edge 603 which responds to differing pressures in the vein 500, to open and close the valve 600. As shown in the figure, the weakened leaflet 502(*a*) may be removed from the vein 500 prior to implantation of the bioprosthetic valve 600. Alternatively, depending on the condition of the weakened leaflet 502(*a*) and its location with respect to the fenestration 502, the weakened leaflet 502(*a*) may be left in the host vein 500.

The bioprosthetic valve 600 is shown in FIG. 6 in a closed position, with the free edge 603 contacting the opposite wall of the host vein 500. However, the free edge 603 need not contact the opposite wall of the host vein 500 continuously, or even at all, in order for the valve to function properly.

The patch 604 may generally match the size and shape of the fenestration 502, and thus may be sutured or otherwise attached to the vein 500 essentially flush with the fenestration 502, as shown in the figure. Alternative embodiments may comprise a patch which is slightly larger than the fenestration, in which case the patch may be sutured or otherwise attached to the host vein in a generally overlapping configuration with the fenestration. Further, as mentioned above, embodiments may include a backing, liner, conduit, or tube secured to the patch. In these and other embodiments, the patch may be indirectly secured to the host vein via the backing, liner, conduit, or tube.

Figure 8:
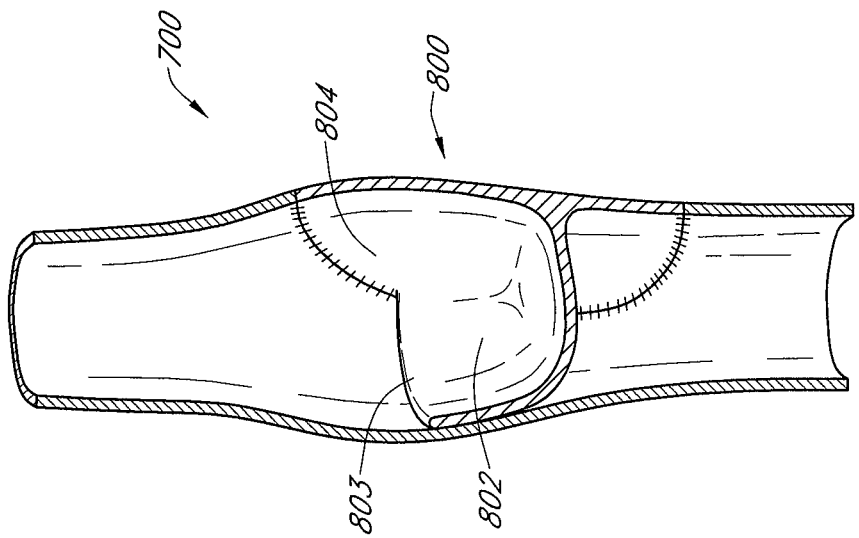
FIG. 8 is a longitudinal cross-sectional view of the host vein of FIG. 7 with an alternative embodiment of the present invention implanted therein.
Figure 7:
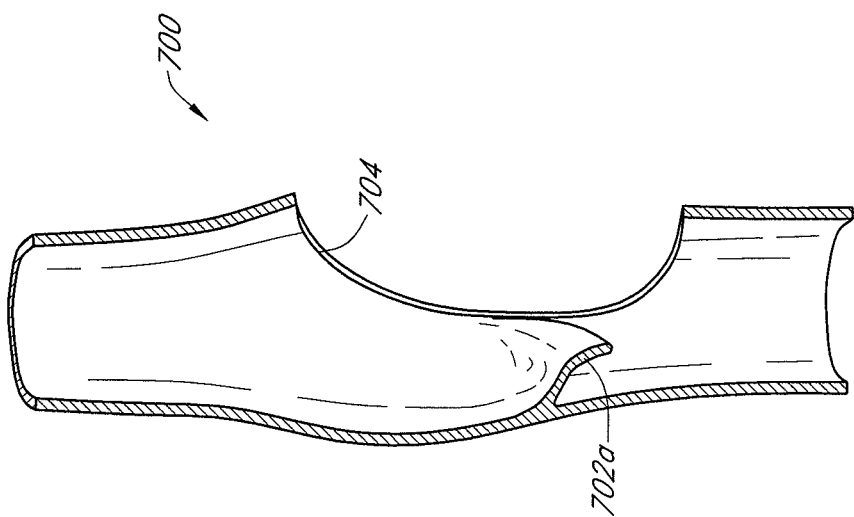
FIG. 7 is a longitudinal cross-sectional view of another vein with a malfunctioning venous valve. The vein is shown with a fenestration in which alternative embodiments of the present invention may be implanted.

Referring now to FIGS. 7-8, another embodiment is illustrated. FIG. 7 shows another malfunctioning vein 700 with a weakened valve leaflet 702(*a*). A portion of the vein 700, including an opposing valve leaflet (not shown), has been excised to create a generally ovoid fenestration 704 in the region of the incompetent valve leaflets. FIG. 8 illustrates the vein 700 having a bioprosthetic valve 800 according to an alternative embodiment implanted therein. The bioprosthetic valve 800 includes a single leaflet 802 from a xenogeneic heart valve attached to a patch 804 of valve wall tissue from the xenogeneic source. The patch 804 has a generally ovoid shape, corresponding to the ovoid shape of the fenestration 704. Providing a generally ovoid or oblong patch 804 may advantageously facilitate suturing and prevent leakage post-implantation.

A method of replacing a malfunctioning venous valve is also provided. From a standard approach, a practitioner may excise a portion of the host vein roughly corresponding in size and shape to a patch of a bioprosthetic valve. Alternative embodiments may incorporate a backing, liner, conduit, or tube attached to the patch, in which case the practitioner may excise a portion of the host vein roughly corresponding to the size and shape of the backing, liner, conduit, or tube. The patch of the bioprosthetic valve may comprise valve wall tissue which is naturally contiguous with a single leaflet of a xenogeneic heart valve. The patch may be attached to the host vein (directly via the valve wall tissue, or indirectly via the backing, liner, conduit, or tube) via suturing or other suitable attachment means in the region of the excised portion.

Depending on the particular circumstances, embodiments can be implanted either above, below, or generally in the region of the incompetent valve being replaced. Any of these embodiments may involve removal of one or more malfunctioning native leaflets prior to implantation of the bioprosthetic valve. Alternatively, depending on the circumstances, the native leaflets may be left in the host vein.

Although standard-approach surgical methods have been described, embodiments of the invention may also be used with minimally invasive techniques. For example, embodiments may be delivered and implanted endovascularly with the aid of an endovascular suturing device. Additionally, a practitioner could make a small inguinal incision and then, with the aid of a scope and a biological glue, secure the biological valve in place.

Embodiments can be used singularly or in multiples throughout the venous system, for example to repair deep vein insufficiencies below the inguinal ligament (i.e., for any vein in the leg) or in the common iliac vein. For example, in larger veins, two bioprosthetic valves according to embodiments may be implanted in opposing relationship to each other on either side of a host vein to create a bileaflet valve geometry. Such a configuration may be used in a region of the host vein away from a region of incompetent valve. To achieve such a bileaflet geometry, two monocusp valves can be implanted separately, with circumferential gaps between the valves. A composited bileaflet or trileaflet valve geometry can also be achieved by attaching together two or three monocusp valves as described above.

Example

Hemodynamic Evaluation of Valve Device

To evaluate the hydrodynamic performance and leaflet motion characteristics of a venous valve device according to the disclosure, several valve devices of various sizes were constructed and tested in the aortic chamber of a pulsatile flow heart valve test apparatus. Hydrodynamic performance was observed under a range of conditions typical of the upper leg of a human being. Leaflet function (i.e., opening and closing) was confirmed for all valve devices under all test conditions studied.

Construction of Valve Devices

Three unconstrained diameters (10 mm, 12 mm, and 14 mm) believed to be suitable for valve devices intended to be implanted in a human vein were selected for evaluation. For each unconstrained diameter, three valve devices were constructed by attaching a gluteraldehyde crosslinked bioprosthetic valve to a support frame by suturing. All specimens were submerged in saline following construction and subjected to irradiation.

Simulation of Compression for Loading into Percutaneous Delivery System

All specimens were loaded into a delivery catheter as shown in the Table I, and held in the compressed delivery configuration for at least 60 (sixty) minutes prior to testing.

TABLE I

Valve device unconstrained diameters and delivery sheath French size for simulation of loading compression

| Valve device unconstrained diameter (mm) | Delivery sheath French size (Fr) |
|---|---|
| 10 | 14 |
| 12 | 16 |
| 14 | 18 |

Test System and Parameters

Each valve device was evaluated in the aortic chamber of a pulsatile flow apparatus from ViVitro Systems, Inc. (Victoria, British Columbia, Canada). Each valve device was sutured into a section of silicone tubing sized so as not to constrain the valve device. Arterial pressure was adjusted to achieve the desired static pressure. Table II provides detailed conditions under which the pulsatile flow analysis was conducted for each valve device.

TABLE II

Pulsatile flow test conditions

| Parameter | Condition |
|---|---|
| Test solution | Physiological saline maintained at 37 ± 1° C. |
| Cycle rate | 30 bbm |
| Cardiac output | 1.2 L/min |
| Static pressure | 15 mmHG ± 1, 35 mmHG ± 1, 50 mmHg ± 1, 100 mmHG ± 1 |
| Single stroke wave form | 70% with leaflet in open position, 30% with leaflet in closed position |

Results

The valve devices were observed visually recorded on video taken from the outflow aspect of the valve device. At least ten measurements of each of the following variables were captured from ten consecutive cycles for each valve device under each static pressure condition: mean pressure difference across the valve device, mean and RMS flow rates through the valve device, stroke volume, cycle rate, mean static pressure over the entire cycle, duration of forward flow through the valve device (as a percentage of cycle time), and regurgitant volume (including the closing, volume, leakage volume, and the corresponding mean pressure difference across the closed valve device).

Also, confirmation of opening and closing of the leaflet of each valve device was made through visual review of video recordings of the pulsatile flow test. Table III presents a summary of the visual confirmations.

TABLE III

Leaflet function based upon review of video recording of pulsatile flow test

| | | Leaflet opening and closing confirmed | | | |
|---|---|---|---|---|---|
| Valve device No. | Diameter (mm) | 15 mmHg | 35 mmHg | 50 mmHg | 100 mmHg |
| 1 | 10 | yes | yes | yes | yes |
| 2 | 10 | yes | yes | yes | yes |
| 3 | 10 | yes | yes | yes | yes |
| 4 | 12 | yes | yes | yes | yes |
| 5 | 12 | yes | yes | yes | yes |
| 6 | 12 | yes | yes | yes | yes |
| 7 | 14 | yes | yes | yes | yes |
| 8 | 14 | yes | yes | yes | yes |
| 9 | 14 | yes | yes | yes | yes |

CONCLUSION

Based on these results, it was concluded that the valve devices made in accordance with the disclosure and tested as detailed above demonstrated acceptable leaflet function over the range of hemodynamic conditions evaluated.

It will be understood by those of skill in the art that numerous and various modifications can be made without departing from the spirit of the present invention. Therefore, it should be clearly understood that the forms of the invention described herein are illustrative only and are not intended to limit the scope of the invention.

What is claimed is:

1. A monocusp bioprosthetic valve for implantation into a host vein of a human subject, comprising a biological tissue from a porcine source having a single leaflet from an aortic heart valve and a patch of tissue contiguous with the single leaflet which includes a natural sinus of said aortic heart valve, wherein said single leaflet from an aortic heart valve is configured to function under low-flow, low-pressure conditions of a human deep venous system, and wherein said patch of tissue is attached to a tube or conduit configured for attachment to a host vein.

2. The monocusp bioprosthetic valve of claim 1, wherein the patch includes a segment of an aortic annulus.

3. The monocusp bioprosthetic valve of claim 1, wherein the single leaflet is a noncoronary leaflet.

4. The monocusp bioprosthetic valve of claim 1, wherein the patch has a generally rectangular shape.

5. The monocusp bioprosthetic valve of claim 1, wherein the patch extends circumferentially on either side of the leaflet so as to provide a region for attachment to said tube or conduit.

6. The monocusp bioprosthetic valve of claim 1, wherein the patch extends axially above and below the leaflet so as to provide a region for attachment to said tube or conduit.

7. The monocusp bioprosthetic valve of claim 1, wherein at least a portion of the patch is covered with a synthetic fabric.

8. The monocusp bioprosthetic valve of claim 1, wherein the subject is human.

9. The monocusp bioprosthetic valve of claim 1, wherein a hemodynamics character of the monocusp bioprosthetic valve matches a hemodynamics character of the human deep venous system.

10. The monocusp bioprosthetic valve of claim 1, wherein the patch further includes a segment of an aortic annulus and a segment of an aortic wall which define a natural sinus for the leaflet.

11. The monocusp bioprosthetic valve of claim 1, wherein the patch includes a portion of an aortic wall which defines a natural sinus for the leaflet.

12. The monocusp bioprosthetic valve of claim 1, wherein the conduit or tube remodels a vessel wall of the host vein.

13. A monocusp bioprosthetic valve for implantation into a host vein of a human subject, consisting essentially of a biological tissue from a porcine source having a single noncoronary leaflet from an aortic heart valve and patch of tissue contiguous with said single noncoronary leaflet which includes a natural sinus of the aortic heart valve, wherein said patch of tissue is attached to a conduit configured for attachment in a host vein, wherein the basic and novel properties include the use of a single porcine noncoronary leaflet that preserves the natural margins of attachment and shape of aortic sinus and is configured to function under low-flow, low-pressure conditions of a human deep venous system.

14. A monocusp bioprosthetic valve for implantation into a host vein of a human subject, consisting of a porcine single noncoronary leaflet from an aortic heart valve and a patch of tissue contiguous with said porcine noncoronary single leaflet including a natural sinus of the aortic heart valve, wherein said contiguous tissue is attached to a conduit or tube.

* * * * *